United States Patent
Jeong et al.

(10) Patent No.: US 9,925,284 B2
(45) Date of Patent: Mar. 27, 2018

(54) NANOPARTICLE COATED WITH LIGAND INTRODUCED WITH LONG HYDROPHOBIC CHAIN AND METHOD FOR PREPARING SAME

(75) Inventors: Jae Min Jeong, Seoul (KR); Young Kyoung Lee, Seoul (KR); Dong Soo Lee, Seoul (KR); June-Key Chung, Seoul (KR); Myung Chul Lee, Seoul (KR)

(73) Assignee: CELLBION CO., LTD., Seoul (KR)

( * ) Notice: Subject to any disclaimer, the term of this patent is extended or adjusted under 35 U.S.C. 154(b) by 151 days.

(21) Appl. No.: 13/982,712

(22) PCT Filed: Jan. 31, 2012

(86) PCT No.: PCT/KR2012/000749
§ 371 (c)(1),
(2), (4) Date: Feb. 18, 2014

(87) PCT Pub. No.: WO2012/105801
PCT Pub. Date: Aug. 9, 2012

(65) Prior Publication Data
US 2014/0199235 A1 Jul. 17, 2014

(30) Foreign Application Priority Data
Feb. 1, 2011 (KR) .................. 10-2011-0010203

(51) Int. Cl.
A61K 51/12 (2006.01)
A61K 49/00 (2006.01)
G01N 33/543 (2006.01)

(52) U.S. Cl.
CPC ...... A61K 51/1244 (2013.01); A61K 49/0067 (2013.01); A61K 49/0089 (2013.01); G01N 33/54346 (2013.01); G01N 33/54353 (2013.01); G01N 33/54393 (2013.01)

(58) Field of Classification Search
CPC combination set(s) only.
See application file for complete search history.

(56) References Cited

U.S. PATENT DOCUMENTS

| 2005/0048570 | A1 | 3/2005 | Weber et al. |
| 2009/0097233 | A1 | 4/2009 | Ooya et al. |
| 2009/0166560 | A1 | 7/2009 | Dai et al. |
| 2011/0064652 | A1* | 3/2011 | Borlak ............... A61K 9/007 424/1.11 |
| 2011/0123439 | A1* | 5/2011 | Cheon ............... A61K 49/0002 424/1.37 |

FOREIGN PATENT DOCUMENTS

| KR | 10-2008-0092870 A | 10/2008 |
| KR | 10-2009-0044293 | 5/2009 |
| WO | WO 2006121590 | 11/2006 |
| WO | WO2007034479 A2 | 3/2007 |
| WO | WO2007097593 A1 | 8/2007 |
| WO | WO 2009097319 A2 * | 8/2009 |

OTHER PUBLICATIONS

Cornelissen, Bart, et al., "In-Labeled Immunoconjugates (ICs) Bispecific for the Epidermal Growth Factor Receptor (EGFR) and Cyclin-Dependent Kinase Inhibitor, p27 Kip1", Cancer Biotherapy and Radiopharmaceuticals, vol. 24, No. 2, 2009, pp. 163-173.
Sharkey, Robert M., et al., "Improved Cancer Therapy and Molecular Imaging with Multivalent, Multispecific Antibodies", Cancer Biotherapy and Radiopharmaceuticals, vol. 25, No. 1, 2010, pp. 1-12.
You, Jun, et al. "Enhancement of Transfection Efficiency Using Ligand-Modified Lipid Vesicles", Journal of Fermentation and Bioengineering, vol. 85, No. 5, 1998, pp. 525-528.
International Search Report for Application No. PCT/KR2012/000749.
Supplemental European Search Report, European Patent Application 12741922.4.
Supplemental European Search Report (European Patent Application 12741922.4).

* cited by examiner

*Primary Examiner* — Robert S Cabral
(74) *Attorney, Agent, or Firm* — John F. A. Earley, III; Frank J. Bonini, Jr.; Harding, Earley, Follmer & Frailey, P.C.

(57) ABSTRACT

The present invention relates to a nanoparticle having a linker connected to a long alkane or alkene chain, and a method for preparing the nanoparticle. The alkyl chain of $C_{10-30}$ introduced with a ligand of the present invention can be coated on a hydrophobic nanoparticle through a noncovalent bond, enabling easy introduction of various ligands to the nanoparticle, and the nanoparticle having various functional groups prepared using the method can be applied to fluorescent detection, MRI, raman spectroscopy, optical detection, PET, SPECT, or gamma image device, and the ligand of the visualization agents can be modified to be used for new vessels detection, cancer cell detection, immunocyte detection, hepatocyte detection, cell death detection, and gene detection.

11 Claims, 8 Drawing Sheets

[Fig. 1]
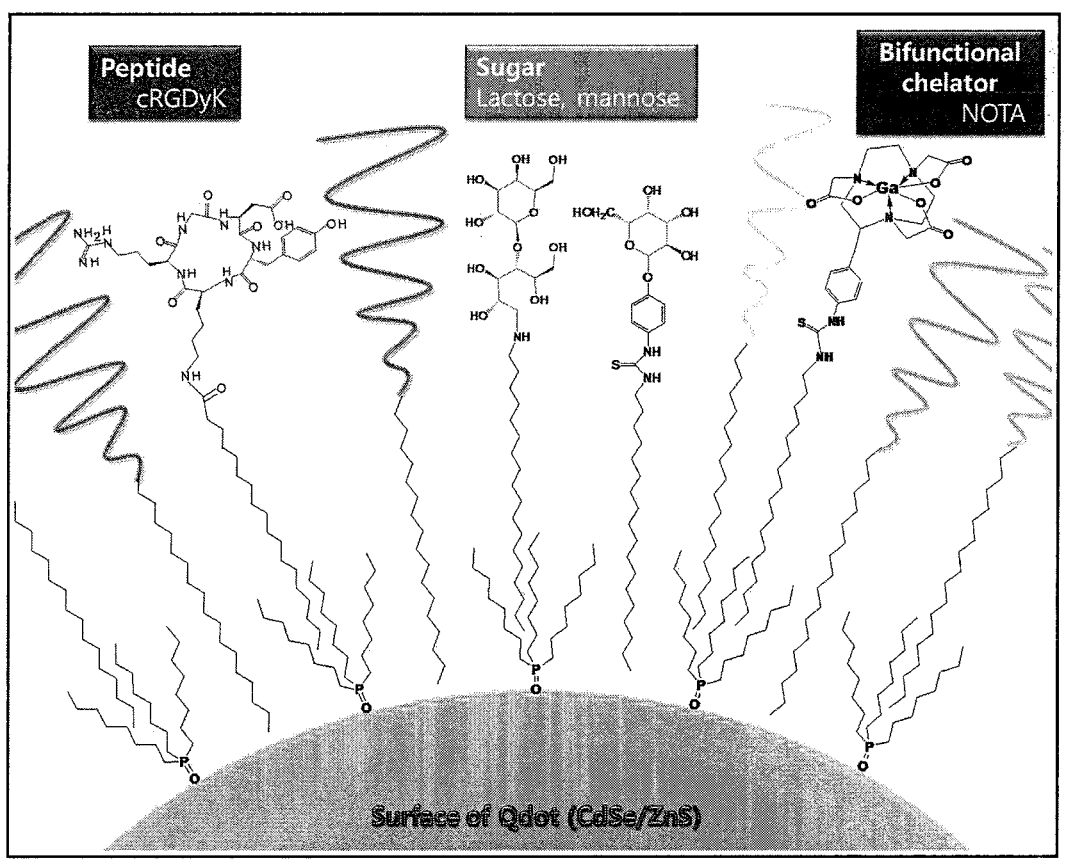

[Fig.2]
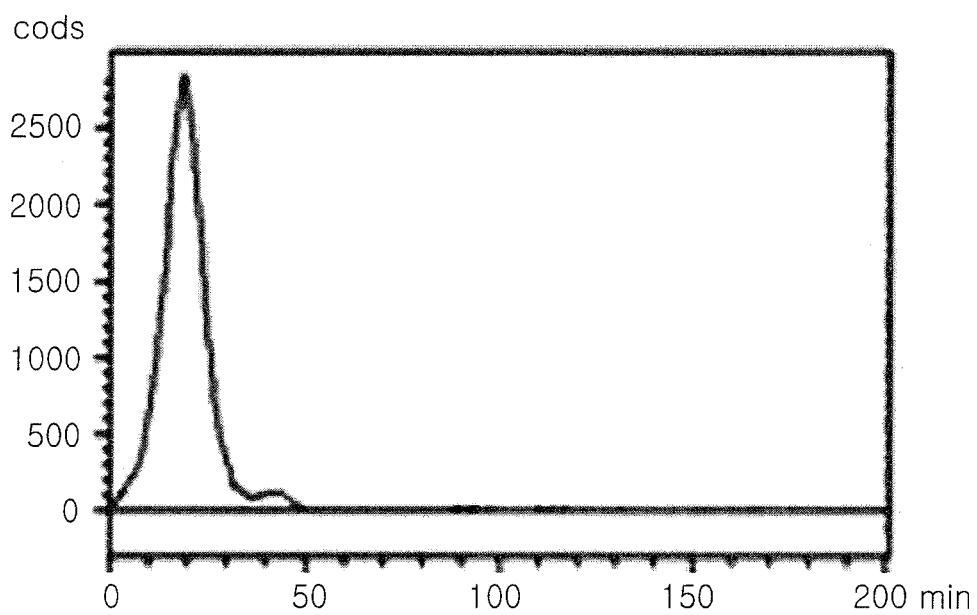
[Fig.3]
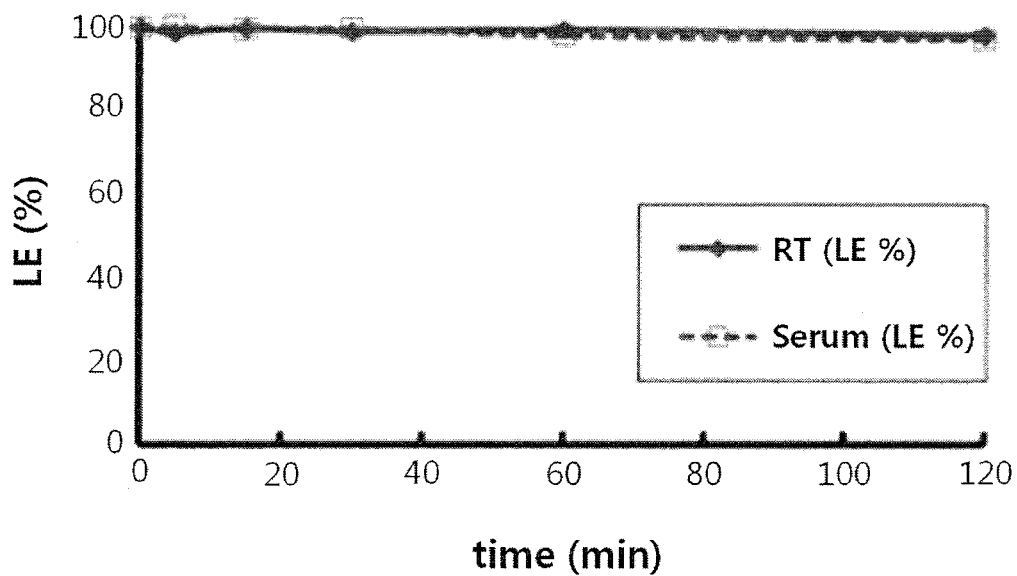

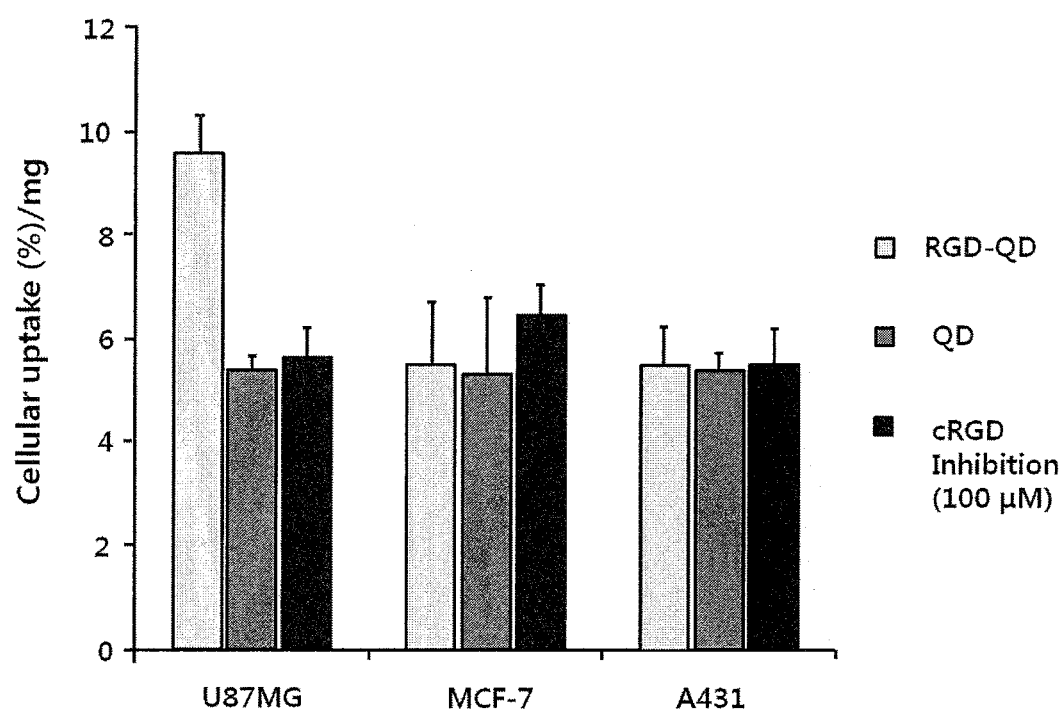
[Fig. 4]

[Fig. 5]
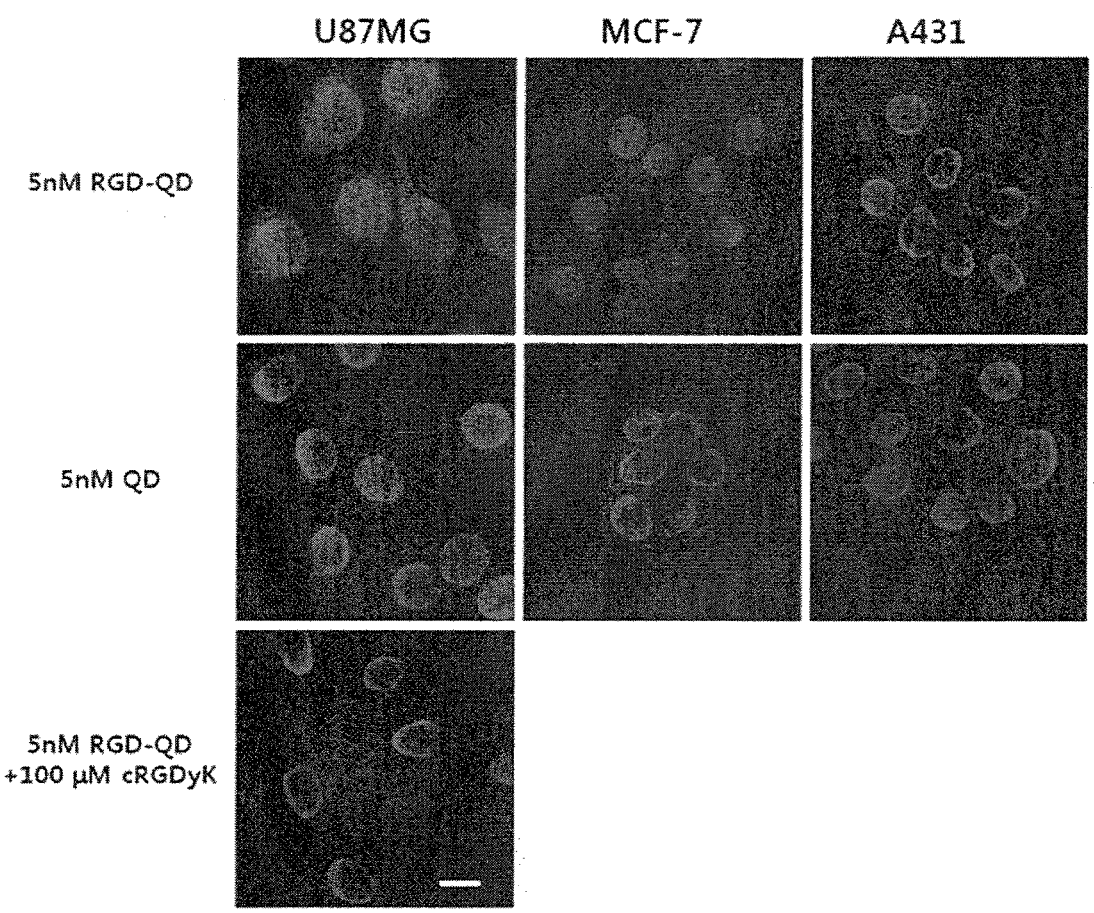

[Fig. 6]
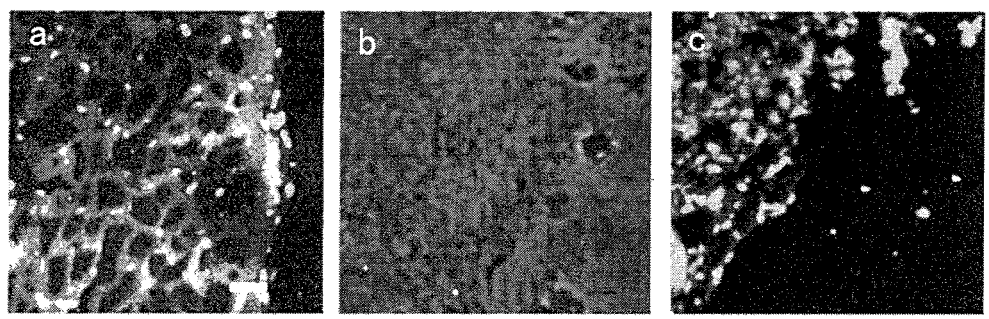
[Fig. 7]
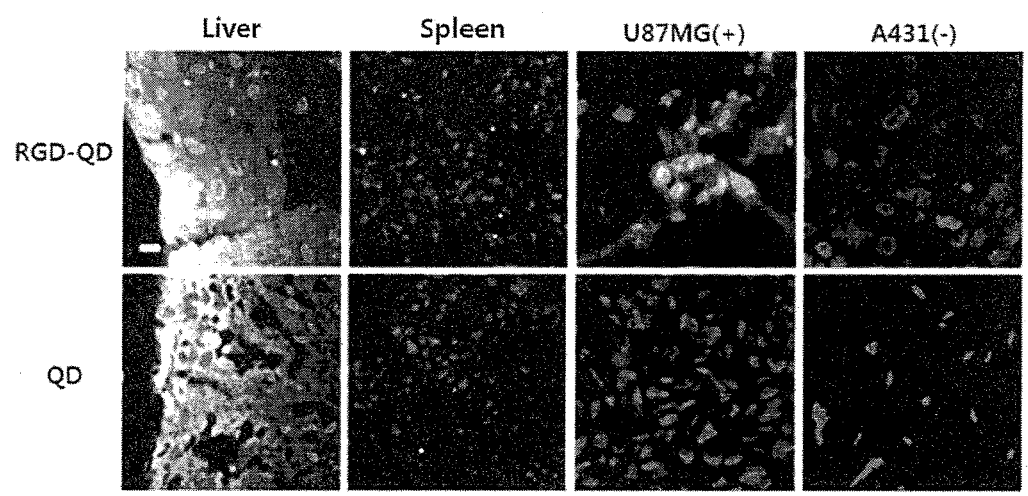

[Fig. 8]
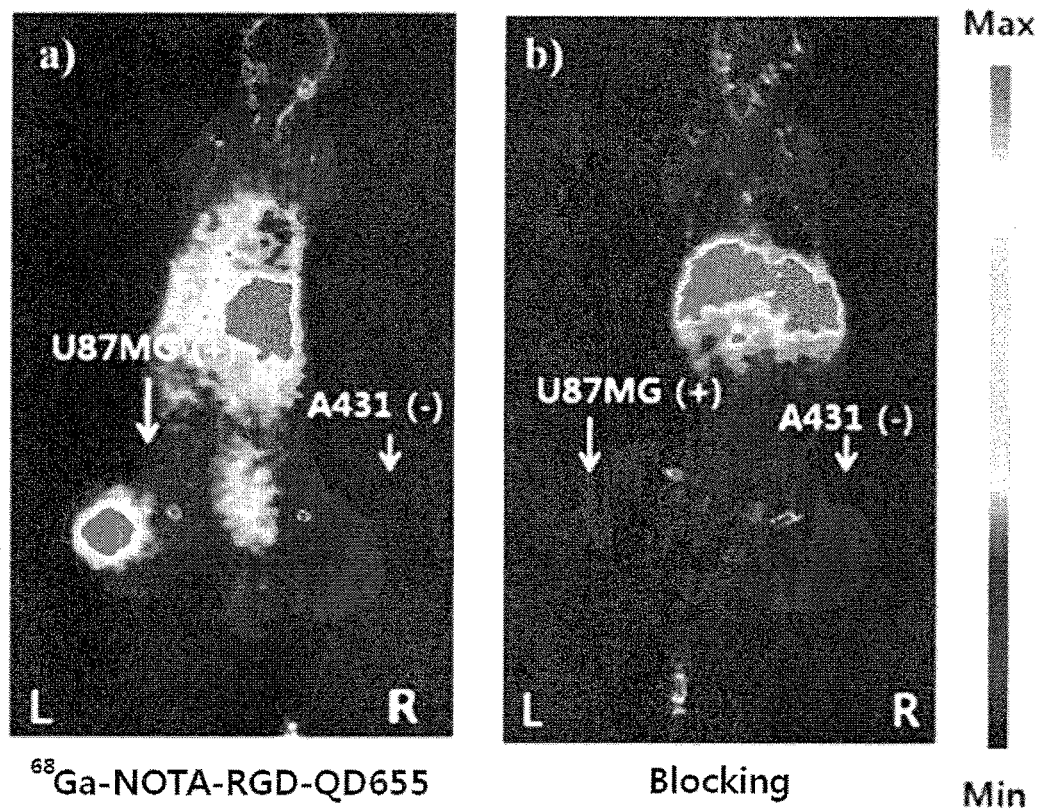

[Fig. 9]
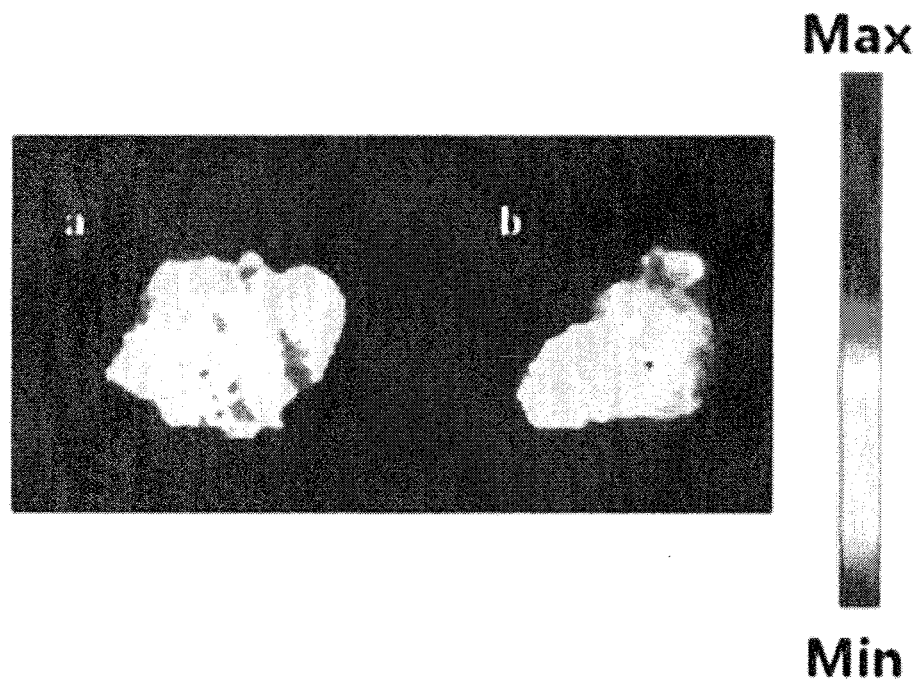
[Fig. 10]
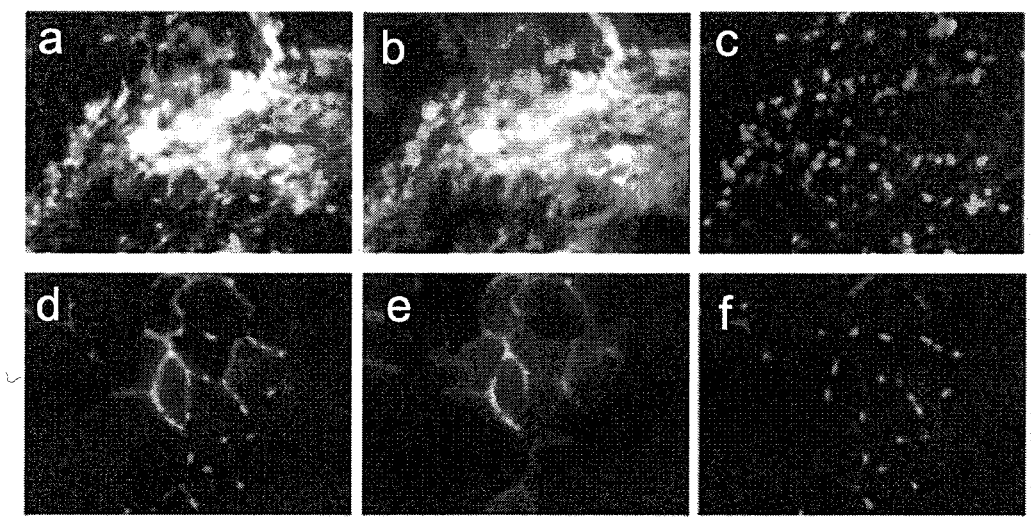

[Fig. 11]
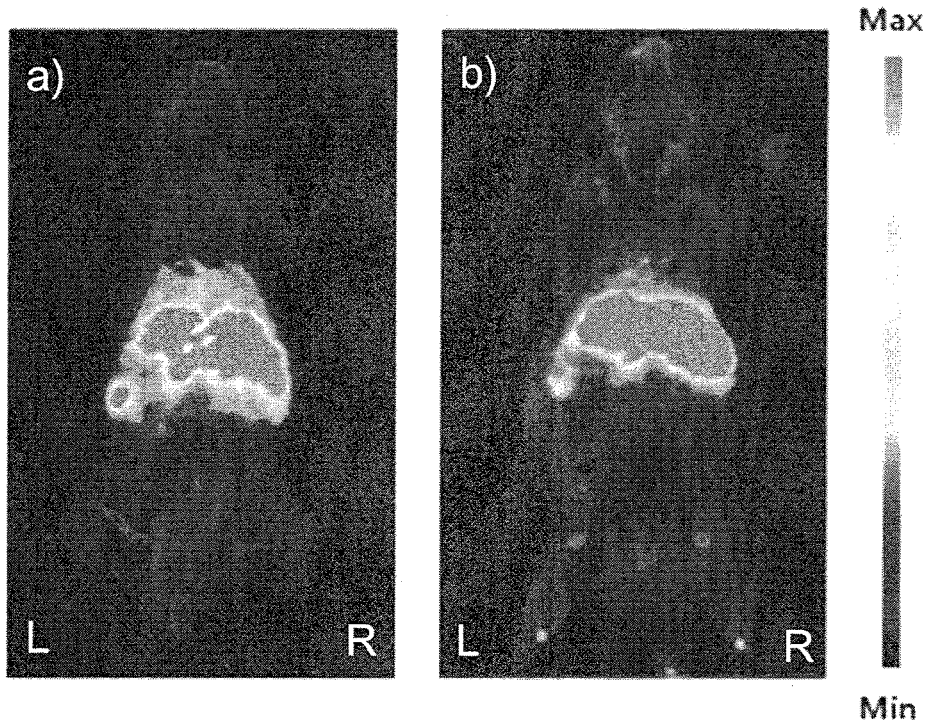
[Fig. 12]
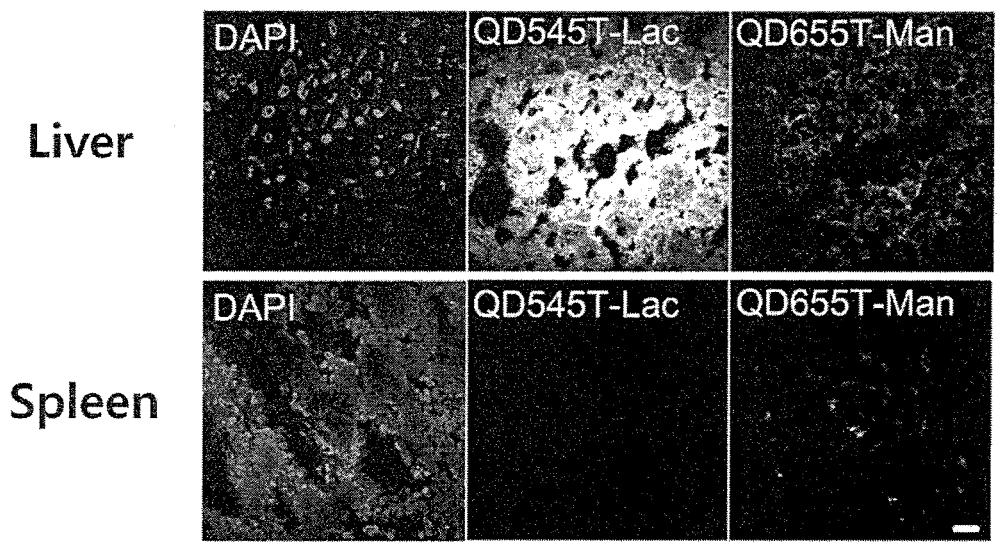

NANOPARTICLE COATED WITH LIGAND INTRODUCED WITH LONG HYDROPHOBIC CHAIN AND METHOD FOR PREPARING SAME

CROSS-REFERENCE TO RELATED APPLICATIONS

This patent application is a U.S. national phase under 35 U.S.C. 371 of PCT/KR2012/000749 filed on Jan. 31, 2012, which claims the benefit of priority from Korean Patent Applications No. 10-2011-0010203 filed on Feb. 1, 2011 in the Korean Intellectual Property Office, the disclosure of which is incorporated herein by reference in its entirety.

BACKGROUND

1. Field of the Invention

The present invention relates to a nanoparticle coated with ligand introduced with a long hydrophobic chain and a method for preparing the same.

2. Description of the Related Art

Nanoparticle refers to a particle whose size is in the range of several nm to several hundred nm. Nanoparticle technology accounts for an important part of nanotechnology as a core technology backing a high-tech industry for the 21st century.

The nanoparticle has particular physical properties—e.g. photic, electrical, and magnetic properties—unlike other bulk particle and thus the nanoparticle produces excellent performances in various applications including electromagnetism, optics, catalysts, sensors, storage, drug delivery system, tissue engineering, diagnostic reagents, and many others. Since the nanoparticle is used in such a wide range of application fields, the technology for preparing the nanoparticle is emerging as a promising technology for the next generation.

Nanoparticle has a growing presence in the medical and pharmaceutical fields, in particular, because the market for the nanoparticle was expected to increase from USD$3.39 billion in 2007 to USD$26 billion in 2012 in the fields, creating a high added value. In addition, the technology for delivering the nanoparticle selectively to a specific tissue, which uses the particular properties of the nanoparticle, is applicable to the body and also usefully applicable to the fields of in-vitro research including tissue staining and cell binding analysis.

Introducing diverse ligands onto the surface of a nanoparticle gives specificity to the nanoparticle for a particular tissue. In addition, introducing two or more different ligands gives the nanoparticle specificity of binding to two or more targets, and thereby enables a specific in-vivo or in-vitro binding to a particular receptor and antigen and provides various detection methods by binding several probes selected from among radioisotopes, optically active materials, and magnetic materials to the nanoparticle.

As the detection methods based on the various conventional detection mechanisms have been widely developed, the nanoparticle probes that may apply several methods and detect various targets simultaneously have been developing.

For example, there has been a report of constructing a bispecific antibody for both epidermal growth factor receptor (EGFR) and cyclin-dependent kinase inhibitor 1 (CDKI) at the same time, attaching first to the surface of a cell and then going into the cell, and attaching to CDK in the cell (Cornelissen B, et al., *Cancer Biother Radiopharm*, 24:163-173, 2009). Also, it has been reported that the bispecific engineered antibody for fragment antigen-binding (Fab) and histamine-succinyl-glycine (HSG) fragment is applied to 2 step imaging (Sharkey R M, et al., *Cancer Biother Radiopharm*, 25:1-12, 2010).

Korean Patent No. 2009-0044293 discloses a nanoparticle for bio-imaging having both bioaffinity and target orientation, which is prepared by partially reforming a part of the surface of the hydrophobic nanoparticle to the hydrophilic one, introducing a desired functional molecule to the hydrophilic group, preparing a functional nanoparticle presenting overall hydrophobicity, and converting the rest part of the nanoparticle surface into the hydrophilic one. In the meantime, Korean Patent No. 2008-0037734 discloses a quantum dot for biocompatible molecular imaging, whose surface is composed of cadmium selenite core and zinc sulfide shell and is attached with cysteamine and water-soluble monosaccharide.

However, the conventional nanoparticle presents hydrophobic property immediately after the preparation and therefore cannot be applied as is to biological or pharmaceutical research conducted mostly under water-soluble condition. Thus, an additional process of introducing residual hydrophilic groups is necessary for the preparation. Moreover, since a nanoparticle is recognized as a foreign substance in the body, it migrates to the reticuloendothelial system immediately after the administration into the body. To prevent this, an additional process of coating polymer such as PEG onto the nanoparticle is required.

In the meantime, such chemical reaction as covalent bond has been mainly performed to introduce diverse ligands to the hydrophilically treated nanoparticle. However, efficiency can deteriorate due to many factors of this chemical reaction including the reaction temperature, pH, presence of impurities, difference of concentration between various reagents, and light. In particular, the error can be severer as the bonding reaction progresses between two or more and thus the variables can be complicated, making the prediction of the reaction harder and reproducibility deteriorate.

Accordingly, the inventors of the present invention have completed the present invention, after finding the method of introducing various ligands to a hydrophobic nanoparticle easily by synthesizing a substance in which a ligand is conjugated with one long alkyl chain and coating the substance onto the hydrophobic nanoparticle through non-covalent bond, in the course of researching on the method of introducing various kinds of ligands, which can be simple and highly recurring for various kinds of hydrophobic nanoparticles.

SUMMARY OF THE INVENTION

The objective of the present invention is to provide a nanoparticle coated with alkyl segment (R) of the compound represented by Formula 1 below on the surface of the hydrophobic nanoparticle through non-covalent bond.

$$R\text{-}A\text{-}L \qquad [\text{Formula 1}]$$

(R, A, and L are as defined herein.)

Another objective of the present invention is to provide a method for preparing a nanoparticle whose surface is coated with the alkyl segment (R) of the compound represented by Formula 1 above, which includes the following steps of adding a hydrophobic nanoparticle into an aqueous solution in which the compound represented by Formula 1 above is dissolved, and dissolving the hydrophobic nanoparticle by selective or combined means of stirring, heating, and ultrasonic irradiating.

Yet another objective of the present invention is to provide an imaging agent using the nanoparticle.

In order to achieve the aforementioned objectives, the present invention provides a nanoparticle which is coated with the alkyl segment (R) represented by Formula 1 on the surface of the hydrophobic nanoparticle through non-covalent bond:

R-A-L [Formula 1]

(In the Formula above, R, A, and L are as defined herein.)

Further, the present invention provides a method for preparing the nanoparticle whose surface is coated with the alkyl segment (R) of the compound represented by Formula 1 above, which includes the following steps of: adding a hydrophobic nanoparticle into aqueous solution in which the compound represented by Formula 1 is dissolved; and dissolving the hydrophobic nanoparticle by selective or combined means of stirring, heating, and ultrasonic irradiating.

Furthermore, the present invention provides an imaging agent using the nanoparticle.

By coating a ligand introduced with the $C_{10-30}$ alkyl chain of the present invention onto a hydrophobic nanoparticle through non-covalent bond, it is easily possible to introduce various ligands to the hydrophobic nanoparticle. Further, the nanoparticle prepared by the method, which has various functional groups, can be applied for the purpose of fluorescent detection, MRI, Raman spectroscopy, optical detection, PET, SPECT, or gamma image device. In addition, by modifying the ligands of the imaging agents, the nanoparticle can preferably be used for the detection of angiogenesis, cancer cells, immunocyte, hepatocyte, apoptosis, and genes.

BRIEF DESCRIPTION OF THE DRAWINGS

FIG. 1 is a schematic view of the nanoparticle according to one example of the present invention.

FIG. 2 is a graph obtained as a result of the instant thin layer chromatography-silica gel (ITLC-SG) analysis on the nanoparticle according to one example of the present invention.

FIG. 3 is a graph showing stability of the isotope-labeled nanoparticle according to one example of the present invention.

FIG. 4 is a graph showing binding force of the nanoparticle according to one example of the present invention.

FIG. 5 are images of fluorescence staining of cells showing the in-vitro cell binding of the nanoparticle according to one example of the present invention.

FIG. 6 are images of fluorescence staining of cells showing the ex vivo cell binding of the nanoparticle according to one example of the present invention.

FIG. 7 are images of fluorescence staining of cells showing the in-vivo cell binding of the nanoparticle according to one example of the present invention.

FIG. 8 are PET images showing the in-vivo distribution of the isotope-labeled nanoparticle in a cancer-transplanted mouse according to one example of the present invention.

FIG. 9 are images of the maestro imaging system showing the in-vivo cell binding of the isotope-labeled nanoparticle in the ischemic model mouse according to one example of the present invention.

FIG. 10 are images of fluorescently stained cells showing the in-vivo cell binding of the isotope-labeled nanoparticle in the ischemic model mouse according to one example of the present invention.

FIG. 11 are PET images of normal mice administered with the isotope-labeled nanoparticle according to one example of the present invention.

FIG. 12 are images obtained as a result of observing the liver and spleen of the normal mouse administered with the isotope-labeled nanoparticle through a fluorescence microscope according to one example of the present invention.

DESCRIPTION OF THE PREFERRED EMBODIMENT

Hereinafter, the present invention will be described in detail.

The present invention provides a ligand introduced with alkyl or alkenyl chain represented by Formula 1 below:

R-A-L [Formula 1]

(In Formula 1,

L denotes a ligand which is selected from the group consisting of amino acid, peptide, protein, nucleic acid, vitamin, hormone, neurotransmitter chelating agent, and saccharide;

A denotes a linker which is selected from the group consisting of —$CH_2$—, —CH=, —C≡, —N—, —NH—, —N=, —O—, —S—, —CS—, —CO—, —$PO_3H$—, —$PO_2H$—, and -benzene-combination;

R denotes $C_{10}$~$C_{30}$ alkyl or alkenyl, in which, if the R is alkenyl, 5 or less double bonds can be contained in the chain.)

Preferably, the L is one or more selected from the group consisting of RGD, cholecystokinin, neurotensin, EGF, VEGF, matrix metalloproteinase (MMP), octreotide, bombesin, TN14003, vasoactive intestinal peptide (VIP), melanocyte stimulating hormone (MSH), substance P, lysine glutamate urea, cysteine, glutamate urea antibody, Pro antibody, antibody fragment, aptamer, folic acid, biotin, IRDye, NOTA, DOTA-SCN, NO2A, DO2A, DO3A, DTPA, HYNIC, iminodiacetate derivatives, or their Ga-68, Ga-67, In-111, Y-90, Lu-177, Tc-99m, Cu-64, I-123, I-124, I-131, Zr-89, Sc-44, and Gd labeled compounds. More preferably, the L is one selected from the group consisting of RGD, NOTA-SCN, DOTA-SCN, lactose, mannose, rhodamine, and indocyanine green.

Preferably, the compound represented by Formula 1 above is one or more selected from the group consisting of cRGDyK-stearate, NOTA-SCN-stearylamine, DOTA-SCN-stearylamine, lactose-stearylamine, mannose-SCN-stearylamine, rhodamine-SCN-stearylamine, and indocyanine green-stearylamine.

Here, RGD is a peptide composed of Arg-Gly-Asp;

cRGDyK is a peptide in a cyclic form of Arg-Gly-Asp-D-Tyr-Lys;

NOTA is 1,4,7-triazacyclononane-1,4,7-triacetic acid;

NOTA-SCN is 2-(p-isothiocyanatobenzyl)-1,4,7-triazacyclononane-1,4,7-triacetic acid;

DOTA is 1,4,7,10-tetraazacyclotetradecane-1,4,7,10-tetraacetic acid;

DOTA-SCN is 2-(p-isothiocyanatobenzyl)-1,4,7,10-tetraazacyclotetradecane-1,4,7,10-tetraacetic acid;

DO2A is 1,4,7,10-tetracyclododecane-1,7-diacetate;

DO3A is 1,4,7-tricarboxymethyl-1,4,7,10-tetraazacyclododecane-1,4,7-triacetic acid;

DTPA is diethylenetriaminepentaacetic acid; and

HYNIC is hydrazinonicotinic acid.

Further, the present invention provides a nanoparticle coated with the alkyl segment (R) of the ligand (R-A-L)

introduced with the alkyl or alkenyl chain onto the surface of the hydrophobic nanoparticle through non-covalent bond.

As shown in FIG. 1, the nanoparticle is bound to the alkyl or alkenyl chain in which the ligand is introduced onto the surface of the nanoparticle. The surface of the nanoparticle may be coated by additionally using a detergent which is not included in Formula 1. The detergent may desirably be Tween 60 or Tween 80.

Since the ligand introduced with the $C_{10\sim30}$ alkyl chain represented by Formula 1 has one tail, it does not form a liposome when dissolved in water, but form a micelle, or has emulsifying action of dissolving oil drops down into nano-size ones, which become the nanoparticle attached with the ligand if the ligand is enclosed with various hydrophobic nanoparticles, instead of the oil drops.

Therefore, the ligand having one alkyl group tail according to the present invention may substitute for various chemical reagents needed for binding a ligand to a nanoparticle through covalent bond.

Further, the present invention provides a method for preparing a nanoparticle whose surface is coated with the alkyl segment (R) of the compound represented by Formula 1 below through non-covalent bond, which includes the following steps of: adding a hydrophobic nanoparticle dissolved in an organic solvent, with the organic solvent removed or remained as is, into the solution in which the compound represented by Formula 1 below is dissolved; and dissolving the hydrophobic nanoparticle by selective or combined means among stirring, heating, and ultrasonic irradiating.

R-A-L  [Formula 1]

(R, A, and L are as defined herein.)

Through the method for preparing the nanoparticle according to the present invention, the nanoparticle with the surface bound with the alkane or alkene in the R segment represented by Formula 1 above and with the ligand in the L segment exposed to the outside may be prepared by evaporating the organic solvent from the hydrophobic nanoparticle dissolved therein or leaving the solvent as is; mixing the nanoparticle with aqueous solution containing therein the compound represented by Formula 1 above, PEG derivative, and a detergent including one long alkane or alkene chain; and dissolving the nanoparticle by selective or combined dissolving means of stirring, heating, and ultrasonically irradiating. The mixed solution prepared as above may be separated by gel-filtration or ultra-filtration, but not limited thereto.

The hydrophobic nanoparticle according to the present invention is selected from nanoparticles having a hydrophobic surface composed of insoluble inorganic matter, and quantum dots may preferably be used. Also, the hydrophobic nanoparticle may be selected from among polymer or dendrimer of organic compounds. Further, if the surface of the prepared organic or inorganic nanoparticle is water-soluble, it is possible to change the surface to be hydrophobic by binding the hydrophobic alkane or alkene chain onto the surface of the nanoparticle through covalent bond.

Preferably, the nanoparticle may be one selected from the group consisting of: semiconductor nanoparticle composed of one element among zinc, cadmium, or lead of Group II on the periodic table and one element among sulfur, selenium, or tellurium of Group VI on the periodic table; metal nanoparticle and metal compound nanoparticle (The metal mentioned herein refers to all the metals belonging to the alkaline earth metals or transition elements on the periodic table, or aluminum, gallium, indium, thallium, germanium, tin, lead, antimony, bismuth, polonium, boron, silicon, or tellurium. Preferably, the metal mentioned herein refers to gold nanoparticle, silver nanoparticle, platinum nanoparticle, iron nanoparticle, iron oxide nanoparticle, manganese oxide nanoparticle, antimony sulfide nanoparticle, or iron sulfide nanoparticle); synthetic organic polymer nanoparticle (PVC, polystyrene, polypropylene, polyethylene, polycarbonate, etc.); dendrimer nanoparticle; polylysine nanoparticle; chitosan nanoparticle; silicon or silicon compound nanoparticle; saccharide nanoparticle; or nanoparticle made from a combination of the above. More preferably, quantum dots may be used.

As for the organic solvent that may be used to dissolve the hydrophobic nanoparticle, volatile solvent such as chloroform, methylene chloride (MC), ethylacetate (EtOAc), ether, acetone, or hexane may be used, and chloroform may preferably be used.

To be specific, the nanoparticle may be obtained by suspending the hydrophobic nanoparticle in chloroform, evaporating the chloroform under a stream of nitrogen, adding aqueous solution containing the compound represented by Formula 1 and the detergent, and stirring strongly at 70° C. for 3 hours.

As shown in FIG. 1, the nanoparticle prepared by the method above is attached to the ligand introduced with the alkane or alkene chain onto the surface of the nanoparticle.

Further, the present invention provides an imaging agent using the nanoparticle.

The imaging agent using the nanoparticle may be used for diagnostic purpose, which is applicable to fluorescent detection, MRI, Raman spectroscopy, optical detection, PET, SPECT, and gamma image device.

Furthermore, the imaging agent is applicable to detection of angiogenesis, cancer cells, immunocyte, hepatocyte, apoptosis, and genes by modifying ligand.

When the nanoparticle of the present invention is labeled with gamma ray or positron emitting nuclides, the nanoparticle may be used as an imaging agent due to a desirable penetrability. If the nanoparticle is labeled with alpha ray or beta ray emitting nuclides, the nanoparticle may be used as a therapeutic agent to kill malignant cells due to a strong destructing property after ionizing molecules.

Further, the nanoparticle of the present invention may be used as a therapeutic agent because the nanoparticle emits secondary radiation such as heat, Auger electron, photoelectron, Compton scattering electron, X-ray, etc. through ultrasonic waves, electromagnetic waves, or particulate radiation applied from the outside and thereby kills malignant cells.

Hereinafter, the present invention will be described in greater detail with examples. But, the following examples are intended only to be illustrative, and not to limit the scope of the claims.

Example 1

Synthesis of RGD-Stearate c(RGDyK) (0.010 g, 0.02 mmol) was dissolved in chloroform (0.5 ml) and triethylamine (TEA; 0.007 ml, 0.05 mmol) was added. After stirring at room temperature for one night, stearoyl chloride (0.015 g, 0.05 mmol) was added, followed by stirring at room temperature for one more night for reaction. The reaction was confirmed to be concluded through mass spectrometry, when the c(RGDyK) peak disappeared and the RGD-stearate peak appeared. The reaction mixture was washed with water, and the organic layer was separated and concentrated. Then, the resulting compound was dissolved again in acetonitrile (1 ml) and recrystallized which gave 8 g of end product. Yield: 57%. Mass spectrum (ESI$^+$), (M+H$^+$): 886.6.

Example 2

Synthesis of NOTA-SCN-Stearylamine 2-(p-isothiocyanatobenzyl)-1,4,7-triazacyclononane-1,4,7-triacetic acid (NOTA-SCN, 0.020 g, 0.04 mmol) was dissolved in chloroform (1 ml) and TEA (0.012 ml, 0.09 mmol) was added, followed by stirring at room temperature. Stearylamine (0.014 g, 0.05 mmol) was added to the reaction mixture and stirred at room temperature for 20 hours. The reaction was confirmed to be concluded through mass spectrometry, when the NOTA-SCN peak disappeared and the NOTA-SCN-stearylamine peak appeared. Then, the resulting compound was recrystallized two times in ether (3 ml×2) which gave 26 mg of end product. Yield: 72%. Mass spectrum (ESI$^+$), (M+H$^+$): 720.5.

Example 3

Synthesis of DOTA-SCN-Stearylamine 2-(p-isothiocyanatobenzyl)-1,4,7,10-tetraazacyclotetradecane-1,4,7,10-tetraacetic acid (DOTA-SCN, 0.020 g, 0.04 mmol) was dissolved in chloroform (1 ml) and TEA (0.015 ml, 0.10 mmol) was added, followed by stirring at room temperature. Stearylamine (0.015 g, 0.06 mmol) was added to the reaction mixture and stirred for one night. The reaction was confirmed to be concluded through mass spectrometry, when the SCN-DOTA peak disappeared and the SCN-DOTA-stearylamine peak appeared. Then, the resulting compound was recrystallized two times in ether (3 ml×2) which gave 23 mg of end product. Yield: 77%. Mass spectrum (ESI$^+$), (M+H$^+$): 821.5.

Example 4

Synthesis of Lactose-Stearylamine

Stearylamine (0.020 g, 0.07 mmol) was dissolved in MeOH (2 ml) and to which α-lactose (0.267 g, 0.74 mmol) dissolved in water (5 ml) was added, followed by stirring desirably at 0° C. The resulting compound was stirred desirably while adding MeOH (1 ml) and sodium cyannoborohydride (0.007 g, 0.11 mmol) dissolved in acetic acid (4 µl) drop by drop. The reaction was confirmed to be concluded through mass spectrometry, when the lactose peak disappeared and the lactose-stearylamine peak appeared. The resulting compound was separated by silica-gel column chromatography (2×5 cm, hexane/ethylacetate), which gave mg of end product. Yield: 68%. Mass spectrum (ESI$^+$), (M+H$^+$): 596.4.

Example 5

Synthesis of Mannose-Stearylamine

α-D-mannopyranosyl-phenylisothiocyanate (0.014 g, 0.04 mmol) was dissolved in chloroform (2 ml), and TEA (0.012 ml, 0.09 mmol) was added and stearylamine (0.012 g, 0.04 mmol) was added, followed by stirring at room temperature. As the reaction proceeded, the cloudy reaction solution became clear. The solution was stirred for 15 hours for reaction. The reaction was confirmed to be concluded through mass spectrometry, when the α-D-mannopyranosyl-phenylisothiocyanate peak disappeared and the mannose-stearylamine peak appeared. Then, the resulting compound was separated by silica-gel column chromatography (2×5 cm, hexane/ethylacetate), which gave 26 mg of end product in a cream-colored solid form. Yield: 77%. Mass spectrum (ESI$^+$), (M+H$^+$): 583.4.

Example 6

Synthesis of Rhodamine-Stearylamine

Rhodamine B-isothiocyanate (0.015 g, 0.03 mmol) was dissolved in chloroform (1 ml) and TEA (0.012 ml, 0.08 mmol) was added, followed by stirring at room temperature for 30 minutes. Stearylamine (0.013 g, 0.04 mmol) was added to the reaction mixture and stirred further for 15 hours for reaction. The reaction was confirmed to be concluded through mass spectrometry, when the rhodamine peak disappeared and the rhodamine-Stearylamine peak appeared. The resulting compound was separated and purified by silica-gel column chromatography (2×5 cm, hexane/ethylacetate), which gave 16 mg of end product in a red-wine color, solid form. Yield: 74%. Mass spectrum (ESI$^+$), (M+H$^+$): 769.5.

Example 7

Synthesis of Indocyanine Green-Stearylamine

Cyanuric chloride (5 mg, 0.0271 mmol) was dissolved in TEA (10 µl, 0.0813 mmol), followed by stirring for approximately 20 minutes in the ice/salt bath to create a solid. Methylene chloride (0.2 ml) was added to the reaction mixture to dissolve the solid, then indocyanine green (22.5 mg, 0.0271 mmol) and stearylamine (7.5 mg, 0.0271 mmol) were added, followed by stirring for 30 minutes further in the ice/salt bath. The resulting compound was analyzed by means of TLC and was separated and purified through silica-gel column chromatography. Yield: 56% (15 mg). Mass spectrum (ESI+), (M+MeCN+): 1044.62.

Example 8

Preparation of PEG-Conjugated Quantum Dot of QD655

Conventional Tween 60 (Tween 60; Sigma-Aldrich) is a surfactant with a hydrophobic stearyl group conjugated onto the head of a hydrophilic PEG. The quantum dots, QD655 and QD545, were purchased from Invitrogen (Carlsbad, Calif., U.S.A.) to use.

QD655 (100 pmol) was evaporated under an inert gas condition to remove the solvent. The dried QD655 was mixed with 2 ml of aqueous solution 4% of the Tween 60, followed by stirring for one night while heating at 70° C. The reaction mixture was separated by flowing boric acid buffer solution through the Sephacryl® S-300 HR column (V0=7.5 ml, Vd=20 ml) purchased from Sigma-Aldrich. The fractions were measured by using a fluorometer and an absorption spectrophotometer.

The coated quantum dot solution was concentrated by means of ultra-filtration (Amicon Ultracel-100 kDa cutoff), and the final concentration was determined by UV-visible ray absorbance. The hydraulic radius and size distribution of the separated coated quantum dot were measured by means of dynamic light scattering (DLS, Malvern Zetasizer Nano ZS90 system, Marlvern Instrument Ltd., U.K.) and transmission electron microscope (TEM, JRM-1400, JEOL, Japan).

The dynamic light measurement was performed after the dilution of the coated quantum dot solution with distilled water and 1 minute of sonication, then the particle size and distribution were obtained based on volume-percent scattered at an angle of 90° at 25° C.

To obtain negative-stain TEM images, a drop of the coated quantum dot solution was dropped onto a carbon-coated copper grid, which was dyed with a saturated uranyl acetate solution, and then the image photographing was made at an accelerating voltage of 80 keV.

Example 9

Preparation of PEG-Conjugated Quantum Dot of QD545

QD545 (100 pmol) was evaporated under an inert gas condition to remove the solvent and was suspended in chloroform (50 μl), then 6% Tween 60 aqueous solution (2 ml) was added, followed by stirring strongly at 70° C. for 3 hours.

The separation and purification of the reaction mixture and the measurement of concentration, hydraulic radius, and size distribution of the reaction mixture were performed by the same method as presented in Example 8 of the coated one.

Example 10

Preparation of RGD-QD655

Except for using 2 ml of 4% Tween 60 aqueous solution containing 5 mol % of the RGD-stearylamine prepared in Example 1, instead of using the 4% Tween 60 of Example 8, the solution was coated onto QD655 and separated by the same method as presented in Example 8 so that RGD-QD655 was prepared.

Example 11

Preparation of NOTA-QD655

Except for using 2 ml of 4% Tween 60 aqueous solution containing 2 mol % of the NOTA-stearylamine prepared in Example 2, instead of using the 4% Tween 60 of Example 8, the solution was coated onto QD655 and separated by the same method as presented in Example 8 so that NOTA-QD655 was prepared.

Example 12

Preparation of NOTA-RGD-QD655

Except for using 2 of 4% Tween 60 aqueous solution containing 5 mol % of the RGD-stearylamine prepared in Example 1 and 2 mol % of the SCN-NOTA-stearylamine prepared in Example 2, instead of using the 4% Tween 60 of Example 8, the solution was coated onto QD655 and separated by the same method as presented in Example 8 so that NOTA-RGD-QD655 was prepared.

Example 13

Preparation of Lac-QD545

Except for using 2 ml of 6% Tween 60 aqueous solution containing 5 mol % of the lactose-stearylamine prepared in Example 4, instead of using the 6% Tween 60 of Example 8, the solution was coated onto QD545 and separated by the same method as presented in Example 8 so that Lac-QD545 was prepared.

Example 14

Preparation of Man-QD655

Except for using 2 ml of 4% Tween 60 aqueous solution containing 2 mol % of the mannose-stearylamine prepared in Example 5, instead of using the 4% Tween 60 of Example 8, the solution was coated onto QD655 and separated by the same method as presented in Example 8 so that Man-QD655 was prepared.

Example 15

Preparation of NOTA-Man-QD655

Except for using 2 ml of 4% Tween 60 aqueous solution containing 2 mol % of the NOTA-stearylamine prepared in Example 2 and 5 mol % of the mannose-stearylamine prepared in Example 5, instead of using the 4% Tween 60 of Example 8, the solution was coated onto QD655 and separated by the same method as presented in Example 8 so that NOTA-Man-QD655 was prepared.

Example 16

Preparation of NOTA-Lac-QD545

Except for using 2 ml of 6% Tween 60 aqueous solution containing 2 mol % of the NOTA-stearylamine prepared in Example 2 and 5 mol % of the lactose-stearylamine prepared in Example 4, instead of using the 6% Tween 60 of Example 8, the solution was coated onto QD545 and separated by the same method as presented in Example 8 so that NOTA-Lac-QD545 was prepared.

Example 17

Preparation of Rhodamine-Iron Oxide Nanoparticle

In a 2 ml glass vial, 5 mg of iron oxide nanoparticle was put and 1 ml of chloroform was added, then ultrasonic waves were applied for 5 minutes for a desirable dispersion. By the same method as presented in Example 8, 2 ml of 4% Tween 60 aqueous solution containing 5 mol % rhodamine-stearylamine prepared in Example 6 was coated onto the iron oxide nanoparticle and separated by Amicon filter so that rhodamine-iron oxide nanoparticle was prepared.

Example 18

Preparation of NOTA-Man-Iron Oxide Nanoparticle

8% Tween 60 solution containing 2 mol % of NOTA-SCN-stearylamine synthesized in Example 2 and 2 mol % of mannose-stearylamine prepared in Example 5 was heated at 80° C., and into which 0.1 ml of chloroform dispersion solution (5 mg/mL) of iron oxide nanoparticle was dropped. Then ultrasonic waves were applied to the solution for 30 minutes to disperse. After heating the solution further for 1 hour at 80° C., ultrasonic waves were applied again for 1 hour to disperse. The reaction mixture was separated and purified by passing through Sephacryl 5500 column so that NOTA-Man-iron oxide nanoparticle was prepared.

Experimental Example 1

Stability Test

Total fluorescence intensity was measured while storing the coated quantum dots prepared as in Examples 8 to 17 at 4° C. for one month. In addition, particle size was measured by using dynamic light scattering (DLS; particle size measurement) and particle forms were observed through a transmission electron microscope (TEM).

As a result of the measurements, it was confirmed to be stable because there were no changes in total fluorescence intensity and particle size.

Experimental Example 2

Radioisotopic Labeling Experiment

After adding 2M sodium acetate buffer solution (300 μl, pH 5.2) to the quantum dot (NOTA-QD655, 50 nM, 100 μl) of Example 11, which was coated with Tween 60 containing 2 mol % of the NOTA-SCN-stearylamine prepared in Example 2, and stirring, $^{68}GaCl_3$ (in 0.5 ml of 0.1 M HCl, 300~500 MBq) was added and reacted at 47° C. for 25 minutes. Labeling efficiency was measured by unfolding an instant thin layer chromatography-silica gel (ITLC-SG) with 0.1 M citric acid solution.

As a result, the non-labeled $^{68}$Ga rose up to the front end of the solvent and the labeled quantum dot remained at the original point, and the labeling efficiency stood at 98% or above. The labeled quantum dot was separated by running physiological saline solution using the NAP-10 column (GE Healthcare, U.S.A.), and radiation was concentrated by using the Amicon filtration apparatus. After the separation, radiochemical purity stood at more than 99%. The result thereof is provided in FIG. 2.

Experimental Example 3

Stability Testing of Radioisotope-Labeled Quantum Dots

To investigate stability of the radioisotope-labeled quantum dot of Experimental Example 4, the following experiment was conducted.

The stability was measured at room temperature for 2 hours after dissolving the Ga-68 labeled $^{68}$Ga-NOTA-QD655 quantum dot in PBS (pH 7.2~7.4, 0.5 ml), and measured at 37° C. for 2 hours after dissolving the Ga-68 labeled $^{68}$Ga-NOTA-QD655 quantum dot in human serum (0.5 ml). Measurement of the radiochemical purity for the stability measurement was conducted under the ITLC-SG condition presented in Experimental Example 2. The result thereof is provided in FIG. 3.

Referring to FIG. 3, the stability stood at over 97% after 2 hours in the PBS (room temperature) and stood at over 96% after 2 hours in the human serum (37° C.).

Based on this, it was confirmed that the $^{68}$Ga-NOTA-QD655 was stable regardless of whether it was left at room temperature or cultured in the serum at 37° C.

Experimental Example 4

In-Vitro Isotope-Labeled Quantum Dot Binding Test

To investigate whether the quantum dot coated with RGD of Example 10 according to the present invention is bound to $\alpha v\beta 3$ integrin, experiments for binding $^{68}$Ga-NOTA-RGD-QD655 and $^{68}$Ga-NOTA-QD655 with U87MG (human glioma cell, strong expression of $\alpha v\beta 3$), A431 (human squamous epithelioma, weak expression of $\alpha v\beta 3$), or MCF-7 (human breast cancer cell, weak expression of $\alpha v\beta 3$) were conducted.

Each cell above was washed with Dulbeco's phosphate buffered saline (DPBS) and was washed once more with a buffer solution (pH 7.4, 20 mM Tris, 150 mM NaCl, 2 mM $CaCl_2$, 1 mM $MnCl_2$, 1 mM $MgCl_2$, 0.1% (wt/vol) bovine serum albumin) for cell binding experiments. Each cell was reacted in the buffer solution (1 ml) containing 0.37 MBq of each labeled quantum dot with 5% carbon dioxide at 37° C. for 15 minutes.

To investigate whether the RGD conjugated quantum dot of Example 10 is selectively taken up in the cells, blocking experiment was conducted at the same time by reacting the $^{68}$Ga-NOTA-RGD-QD655 containing cRGDyK (10 μM). The culture medium was removed to stop the cellular uptake, then three times of washing with cooled DPBS followed. After dissolving the cells in 1% SDS solution (0.5 ml/well), radiation was measured by a gamma counter. The amount of protein was measured by using BCA (BCA Protein assay kit, Pierce) to standardize radiation uptake to uptake rate per mg of protein. The result thereof is provided in Table 1 and FIG. 4.

TABLE 1

| | Cellular Uptake Rate (%) | | |
|---|---|---|---|
| | RGD-QD (Ex. 10) | QD (Control Group) | cRGD inhibition (100 μM) (Comparison Group) |
| U87MG (glioma cell) | 9.64 ± 0.70 | 5.47 ± 0.25 | 5.65 ± 0.59 |
| MCF-7 (squamous epithelioma cell) | 5.57 ± 1.15 | 5.36 ± 1.44 | 6.51 ± 0.54 |
| A431 (breast cancer cell) | 5.50 ± 0.76 | 5.44 ± 0.30 | 5.57 ± 0.66 |

As shown in Table 1 above and FIG. 4, the $^{68}$Ga-NOTA-RGD-QD655 was bound exclusively to the U87MG cell expressing $\alpha v\beta 3$ integrin, but not to other cells. When blocking with cRGD, the $^{68}$Ga-NOTA-RGD-QD655 was not bound even to the U87MG cell, showing that the $^{68}$Ga-NOTA-RGD-QD655 was not bound to any cell lines.

Experimental Example 5

In-Vitro Fluorescence Staining Experiment on Quantum Dot Cells

To obtain confocal images of the quantum dots according to the present invention, $1.5 \times 10^4$ cell/chamber cells were spread out on an 8-well glass chamber slide (Lab-Tek Chamber Slide System, Nalge Nunc International) one day before conducting the experiment.

After the cells were stabilized, the cells were washed with a warm experimental cell-binding buffer solution. The buffer solution containing 50 nM each of the PEG-QD655 of Example 8 or the RGD-QD655 of Example 10 was applied 200 μl to each cell and allowed to react for 15 minutes. After concluding the reaction by removing the cell-binding buffer solution, the cells were washed with the cooled DPBS three times. After fixing the cells with 3.7% paraformaldehyde solution, the cells were mounted with DAPI solution. The result thereof is provided in FIG. 5.

Referring to FIG. 5, the RGD-QD655 of Example 10 was bound exclusively to the U87MG cell expressing $\alpha v\beta 3$ integrin, but the PEG-QD655 of Example 8 was not bound to any cells. The binding of the RGD-QD655 of Example 10 to the U87MG was blocked by cRGDyK.

Experimental Example 6

In-Vitro Fluorescence Staining Experiment on Quantum Dot Tissues

U87MG ($2\times10^5$ cells/0.1 ml) was injected hypodermically into femoral region of a Balb/c nude mouse to make a tumor model. When the tumor size reached 1 cm$^3$ or larger, the tumor tissue was made into a 7 μm frozen section at −20° C. After attaching the section onto the slide glass, it was fixed with acetone at −20° C. for 20 minutes. The section was cultured in the 10% (v/v) fetal bovine serum at room temperature for 30 minutes, to which the RGD-QD655 (30 nM, 100 ml) of Example 10 was added, then cultured at 4° C. for one night to conduct fluorescence staining. cRGdyK (500 nM) was added one minute before binding the RGD-QD655 of Example 10 to conduct the blocking experiment. To observe the nucleus through a confocal microscope, the section was mounted with DAPI solution. The QD655, and the DAPI and QD545 were scanned by a 488 nm laser and 405 nm laser, respectively, to obtain confocal images. The result thereof is provided in FIG. 6.

Referring to FIG. 6, the RGD-QD655 of Example 10 was bound to the U87MG tumor tissue expressing the $\alpha v\beta 3$ integrin (a). On the contrary, the PEG-QD655 of Example 8 was not bound (b). However, the binding of the RGD-QD655 of Example 10 to the U87MG was blocked by cRGDyK (c).

Experimental Example 7

In-Vivo Fluorescence Staining Experiment on Quantum Dot Tissues

U87MG ($2\times10^5$ cells/0.1 ml) and A431 ($1\times10^7$ cells/0.1 id) cells were injected hypodermically into both femoral regions of a Balb/c nude mouse to make a tumor. The RGD-QD655 (120 nM, 0.1 ml) of Example 8 was injected intravenously into a tail vein of the mouse with the tumor. Meanwhile, the PEG-QD655 (127 nM, 0.1 ml) of Example 8 was injected to a negative controller. One hour after the injection, the mouse was sacrificed to extract the organs, to which incident light was applied using a yellow filter to obtain fluorescent images by using the maestro imaging system.

Further, the tumor was put into OCT medium (Tissue-Tek O.C.T. compound, Sakura, Finetek) to obtain a 7 μm-thick frozen section. The section was attached onto a slide glass, fixed with 3.7% (v/v) paraformaldehyde solution, and mounted with DAPI solution. The section was observed through a confocal microscope. The result thereof is provided in FIG. 7.

Referring to FIG. 7, the RGD-QD655 of Example 10 was absorbed into the U87MG tumor tissue expressing the $\alpha v\beta 3$ integrin during the intravenous injection, but was not absorbed into the A431 tumor tissue not expressing the $\alpha v\beta 3$ integrin. On the contrary, the PEG-QD655 of Example 8 was not absorbed into any tumor tissues.

Experimental Example 8

Isotope-Labeled Quantum Dot PET

As presented in Experimental Example 2, the Ga-68 labeled $^{68}$Ga-NOTA-RGD-QD655 (30~40 MBq in 0.1 ml normal saline) was injected intravenously into a tail vein of the mouse with the growing U87MG cancer cell. One hour after the injection, the mouse was anesthetized by isoflurane to perform PET. For blocking experiment, cRGDyK (1 mM) was concurrently injected. The result thereof is provided in FIG. 8.

Referring to FIG. 8, the RGD-QD655 of Example 10 was absorbed into the U87MG tumor tissue expressing the $\alpha v\beta 3$ integrin during the intravenous injection, but not absorbed into the A431 tumor tissue not expressing the $\alpha v\beta 3$ integrin. However, the RGD-QD655 was absorbed mainly into the liver among normal tissues (a). In the case of the concurrent injection of the cRGDyK, the RGD-QD655 was not absorbed into the two tumor tissues either, but absorbed into the liver (b).

Experimental Example 9

In-Vivo RDG-QD655 Binding Experiment on Model Mice with Ischemia on Hind Leg

To investigate whether the $\alpha v\beta 3$ expressed in an ischemic tissue of the RGD-QD655 quantum dot of Example 10 is bound or not, the following experiment was conducted.

A left femoral artery of a ten week-old ICR mouse was tied up to make an ischemic model on the hind leg. One week after the tied-up, the RGD-QD655 (50 nM, 0.15 ml) of Example 10 was injected intravenously into a tail vein of the mouse. The ischemic femoral muscle and the opposite-side femoral muscle were cut off to observe the fluorescence by using the maestro imaging system.

Further, the tissue was sliced into a frozen section (7 μm). After staining the section with DAPI, the section was observed through a fluorescence microscope. For a negative controller, the PEG-QD655 of Example 8 was used. The result thereof is provided in FIG. 9.

Referring to FIG. 9, the RGD-QD655 of Example 10 was absorbed more into the ischemia-induced muscle (a) than the normal muscle (b) as a result of the observation of fluorescence by using the maestro imaging system after the intravenous injection and the cut-off of the muscles. This shows that the $\alpha v\beta 3$ integrin was expressed as a new blood vessel was formed in the ischemia-induced tissue.

Referring to FIG. 10, the ischemia-induced tissue (a, b, c) appeared fluorescent more deeply than the tissue to which ischemia was not induced (d, e, f) as a result of the observation of the ischemia-induced tissue and normal tissue through a fluorescence microscope.

Here, a and d were overlaps of fluorescence and DAPI images; b and e showed fluorescent images; and c and f showed DAPI images.

Experimental Example 10

PET Images of Normal Mouse Administered with $^{68}$Ga-NOTA-Man-QD655 and $^{68}$Ga-NOTA-Lac-QD545

It is reported that a number of Kupffer cells having mannose receptor are present in the liver and spleen. It is also reported that since there are many galactose receptors in the hepatocyte, the mannose conjugated nanoparticles are largely absorbed into the liver and spleen and the galactose conjugated nanoparticles are largely absorbed into the liver. Further, it is reported that since lactose contains galactose, the lactose conjugated nanoparticles are largely absorbed into the liver. Based on the reports, the following experiment was conducted to measure the PET images of the mouse administered with the $^{68}$Ga-NOTA-Man-QD655 and $^{68}$Ga-NOTA-Lac-QD545 quantum dots.

The NOTA-Man-QD655 and NOTA-Lac-QD655 prepared in Examples 15 and 16 were labeled with Ga-68 by the method presented in Experimental Example 2. The $^{68}$Ga-NOTA-Man-QD655 (10.36 MBq/0.15 ml) and $^{68}$Ga-NOTA-Lac-QD545 (14.8 MBq/0.08 ml) were injected intravenously into a tail vein of a normal ICR mouse. Thirty minutes after the intravenous injection, PET-CT imaging was performed. The result thereof is provided in FIG. 11.

Referring to FIG. 11, after observing the overlapped PET with CT images of the mouse injected with the $^{68}$Ga-NOTA-Man-QD655 and $^{68}$Ga-NOTA-Lac-QD545 according to the present invention, the $^{68}$Ga-NOTA-Man-QD655 was absorbed into the liver and spleen (a). On the contrary, the $^{68}$Ga-NOTA-Lac-QD545 was absorbed mainly into the liver but absorbed lower into the spleen.

Experimental Example 11

Fluorescence Microscope

Observation of Liver and Spleen Tissues of Normal Mouse administered concurrently with NOTA-Man-QD655 and NOTA-Lac-QD545

The Man-QD655 (70 nM, 30 μl) and Lac-QD545 (70 nM, 120 μl) prepared in Examples 13 and 14, respectively, were mixed together. The mixture was injected intravenously into a tail vein of a 6 week-old normal ICR mouse. Twenty minutes after the intravenous injection, the mouse was sacrificed to extract the liver and spleen. After putting the extracted liver and spleen into OCT compound and freezing at −20° C., a 7 μm-thick frozen section was made and stained by DAPI solution to observe the section through a fluorescence microscope. The result thereof is provided in FIG. 12.

Referring to FIG. 12, the blue DAPI showed the distribution of liver nuclei, the green Lac-QD545 was absorbed into hepatocyte taking up most of the liver and not absorbed into the spleen. Further, the red Man-QD655 was absorbed by Kupffer cells which are much less than hepatocyte.

Therefore, the nanoparticle according to the present invention can be applied to fluorescent detection, MRI, raman spectroscopy, optical detection, PET, SPECT, or gamma image device. Further, by modifying the ligand of the imaging agents, the nanoparticle can be used for detection of angiogenesis, cancer cells, immunocyte, hepatocyte, apoptosis, or genes.

What is claimed is:

1. A nanoparticle, wherein a substance having an alkyl or alkenyl group R linked to a ligand L via a linker A and having a structure consisting of Formula 1 below is coated onto a surface of a hydrophobic nanoparticle via a non-covalent bond between the hydrophobic nanoparticle and an alkane chain or an alkene chain of the alkyl or alkenyl group R:

$$R\text{-}A\text{-}L \qquad \text{[Formula 1]}$$

where,

L is a ligand selected from the group consisting of amino acid, peptide, protein, nucleic acid, vitamin, hormone, neurotransmitter, saccharide, chelating agent, and fluorescent dye, A is a linker selected from the group consisting of —CH$_2$—, —CH=, —N—, —NH—, —N=, —O—, —S—, —CS—, —CO—, —PO$_4$H—, —PO$_3$H—, —PO$_2$H—, and -benzene-, and R is a $C_{10}$~$C_{10}$ alkane or a $C_{10}$~$C_{30}$ alkene, and wherein if the R is an alkene, 5 or less double bonds are contained in the chain.

2. The nanoparticle according to claim 1, wherein the L is one or more selected from the group consisting of RGD, cholecystokinin, neurotensin, EGF, VEGF, matrix metalloproteinase (MMP), octreotide, bombesin, TN14003, vasoactive intestinal peptide (VIP), melanocyte stimulating hormone (MSH), Substance P, lysine glutamate urea, cysteine glutamate urea, antibody, antibody fragment, aptamer, folic acid, biotin, NOTA, DOTA-SCN, NO2A, DO2A, DO3A, DTPA, HYNIC, iminodiacetate derivative, or their Ga-68, Ga-67, In-111, Y-90, Lu-177, Tc-99m, Cu-64, I-123, I-124, I-131, Zr-89, Sc-44, Gd labeled compound, galactose, lactose, mannose, rhodamine, indocyanine green, Cy3, Cy3.5, Cy5, Cy5.5, Cy7, Cy7.5, Alexa Fluor, Oregon Green, Pacific Blue dye, and IRDye.

3. The nanoparticle according to claim 1, wherein the hydrophobic nanoparticle is selected from the group consisting of semiconductor nanoparticle comprising one element consisting of zinc, cadmium, and lead and one element selected from the group consisting of sulfur, selenium, and tellurium; metal nanoparticle and metal compound nanoparticle; silicon or silicon compound nanoparticle; synthetic organic polymer nanoparticle; dendrimer nanoparticle; polylysine nanoparticle; chitosan nanoparticle; saccharide nanoparticle; or nanoparticle comprising a combination of the above.

4. The nanoparticle according to claim 1, wherein the surface of the hydrophobic nanoparticle is coated further with PEG derivative and an alkane or alkene group of a detergent comprising PEG derivative and one long alkane or alkene chain, wherein one long alkane or alkene chain in detergent coats the surface of the nanoparticle through non-covalent bond.

5. A method for preparing a nanoparticle, wherein a substance having an alkyl or alkenyl group R linked to a ligand L via linker A and having a structure consisting of Formula 1 below is coated onto a surface of a hydrophobic nanoparticle via a non-covalent bond between the hydrophobic nanoparticle and an alkane chain or an alkene chain of the alkyl or alkenyl group R, the method comprising the following steps of:

mixing a hydrophobic nanoparticle dissolved in organic solvent, with the organic solvent either removed or retained, with aqueous solution comprising a substance, PEG derivative, and a detergent comprising one long alkane or alkene chain, wherein the substance has a structure consisting of Formula 1 below; and dispersing the mixture by selective or combined dissolving means of stirring, heating, and irradiating;

Formula 1 being as follows:

$$R-A-L \quad \text{[Formula 1]}$$

where,

L is a ligand selected from the group consisting of amino acid, peptide, protein, nucleic acid, vitamin, hormone, neurotransmitter, saccharide, chelating agent, and fluorescent dye, A is a linker selected from the group consisting of —$CH_2$—, —CH=, —N—, —NH—, —N=, —O—, —S—, —CS—, —CO—, —$PO_4H$—, —$PO_3H$—, —$PO_2H$—, and -benzene-, and R is a $C_{10}$~$C_{30}$ alkane or a $C_{10}$~$C_{30}$ alkene, and wherein if the R is alkene, 5 or less double bonds are contained in the chain.

6. The method according to claim 5, wherein the hydrophobic nanoparticle is selected from the group consisting of semiconductor nanoparticle comprising one element selected from the group consisting of zinc, cadmium, and lead and one element selected from the group consisting of sulfur, selenium, and tellurium; metal nanoparticle and metal compound nanoparticle; silicon or silicon compound nanoparticle;

synthetic organic polymer nanoparticle; dendrimer nanoparticle; polylysine nanoparticle; chitosan nanoparticle; polysaccharide nanoparticle; or nanoparticle comprising a combination of the above.

7. An imaging agent using the nanoparticle of claim 1.

8. The imaging agent according to claim 7, wherein the imaging agent is applicable to fluorescent detection, MRI, Raman spectroscopy, optical detection, PET, SPECT, or gamma image device.

9. The imaging agent according to claim 7, wherein the image agent is applicable to detection of angiogenesis, cancer cells, immunocyte, hepatocyte, apoptosis, or genes, by modifying ligand.

10. A therapeutic agent using the nanoparticle of claim 1, wherein the therapeutic agent kills malignant cells by emitting alpha ray or beta ray, or emitting heat or secondary radiation after absorbing ultrasonic waves, electromagnetic waves, or particulate radiation applied from outside.

11. The nanoparticle according to claim 1, wherein the surface of the hydrophobic nanoparticle is coated further with detergent comprising a PEG segment and an alkane or alkene segment, wherein the alkane or alkene segment of a surface of nanoparticle is non-covalently bonded with the alkyl or alkenyl group of the substance having the structure of Formula 1.

* * * * *

UNITED STATES PATENT AND TRADEMARK OFFICE
CERTIFICATE OF CORRECTION

PATENT NO. : 9,925,284 B2
APPLICATION NO. : 13/982712
DATED : March 27, 2018
INVENTOR(S) : Jae Min Jeong et al.

It is certified that error appears in the above-identified patent and that said Letters Patent is hereby corrected as shown below:

In the Claims

Claim 1, Line 15: "-$CH_2$-, -CH=," should read -- "-$CH_2$-, -CH=, -C≡ --.

Claim 1, Line 18: "R is a $C_{10}$~$C_{10}$ alkane" should read -- R is a $C_{10}$~$C_{30}$ alkane --.

Claim 5, Line 25: "-$CH_2$-, -CH=," should read -- "-$CH_2$-, -CH=, -C≡ --.

Claim 6, Lines 1-12: Claim 6 should be a single paragraph and should read as:
-- 6. The method according to claim 5, wherein the hydrophobic nanoparticle is selected from the group consisting of semiconductor nanoparticle comprising one element selected from the group consisting of zinc, cadmium, and lead and one element selected from the group consisting of sulfur, selenium, and tellurium; metal nanoparticle and metal compound nanoparticle; silicon or silicon compound nanoparticle; synthetic organic polymer nanoparticle; dendrimer nanoparticle; polylysine nanoparticle; chitosan nanoparticle; polysaccharide nanoparticle; or nanoparticle comprising a combination of the above. --.

Signed and Sealed this
Thirtieth Day of October, 2018

Andrei Iancu
*Director of the United States Patent and Trademark Office*